United States Patent
Yelvington

[11] Patent Number: 5,874,054
[45] Date of Patent: Feb. 23, 1999

[54] DEVICE FOR ENCAPSULATION OF PLASTIC SYRINGES

[75] Inventor: Richard Yelvington, Jacksonville, Fla.

[73] Assignee: Imagination Medical, Inc., Jacksonville, Fla.

[21] Appl. No.: 659,906

[22] Filed: Jun. 7, 1996

[51] Int. Cl.⁶ .............................. B01B 9/00; B01D 9/00; B23H 1/00; B29C 11/08

[52] U.S. Cl. ........................... 422/309; 219/68; 264/294; 264/320

[58] Field of Search .............................. 422/309; 219/68; 264/294, 320

[56] References Cited

U.S. PATENT DOCUMENTS 5,411,697  5/1995  McGraw ............................ 264/294
5,489,200  2/1996  McGraw ............................ 425/144

Primary Examiner—Lynette F. Smith
Attorney, Agent, or Firm—Thomas C. Saitta

[57] ABSTRACT

A device for encapsulating plastic waste such as plastic syringes with attached needles, lancets or blood test strips, having a melt chamber to receive the waste, means to elevate the temperature within the melt chamber, a reciprocating compaction head to compact the melted waste to form a plastic slug with the needles encapsulated within the slug, where the compaction head has a shoulder whereby the slug becomes attached to the compaction head when hardened. The hardened slug is then removed from the melt chamber during the retraction of the compaction head. Preferably, an ejection cam slides the plastic slug partially off the compaction head for easy removal.

17 Claims, 7 Drawing Sheets

DEVICE FOR ENCAPSULATION OF PLASTIC SYRINGES

BACKGROUND OF THE INVENTION

This invention relates generally to the field of devices for the destruction, encapsulation or disposal of potentially hazardous plastic waste, especially such waste comprising used medical syringes with attached needles or lancets. More particularly, the invention relates to such devices which melt and compact the plastic waste to completely encapsulate the needles into a sterile, disposable slug.

It is necessary to dispose of used medical syringes, lancets and blood test strips in a manner which minimizes the possibility of injury or infection to persons handling the syringes, at the initial point of use and disposal as well as all along the handling chain to final disposition in a land fill or the like. Numerous methods or devices have been developed to address this problem. Some such devices provide means to cap or enclose the needle, but enclosure of the needle by a physical housing requires the person to perform an additional physical act where inadvertent contact is possible and does not address the need to sterilize the syringes to kill infectious organisms. Devices are also known which provide protection from the syringe needles by melting the plastic portions of the syringes such that the needles are encased in the resulting plastic mass. This technique is an improvement over the capping method, since the used needle is simply deposited into the disposal device with minimal handling. The temperature achieved within the melt chambers of these devices is greater than that required to melt the plastic in order to also sterilize the waste material.

Examples of such combination disposal and sterilization devices are shown in U.S. Pat. No. 4,800,958 to Yerman and in U.S. Pat. No. 5,207,994 to Suziki. These devices provide a cylindrical melting chamber with a reciprocating piston. The waste syringes are placed into the chamber, heated and compressed to form a puck or slug to encapsulate the needles. The plastic slug is then removed by opening separate access plates or doorways and disposed of.

Both of these devices, as well as all other similar known devices, involve multiple joints, doorways, hinges and other components which are susceptible to fouling from plastic flash. Plastic flash is molten plastic which escapes from the melting chamber due to the effects of gravity or pressure from the compacting piston. Syringe plastic contains paraffin, which becomes a highly viscous liquid at temperatures well below those required to sterilize the plastic waste. The sterilization step requires temperatures in excess of 350 degrees F. to achieve sterilization in a relatively short time period. During the melting process, at about 275 degrees F., the paraffin becomes a highly viscous liquid which is forced past the seals and joints in the known devices. To counter this, highly efficient seals and joints must be constructed with very tight precision. These air and fluid tight seals prevent the escape of water vapor, steam and other outgas products produced during the melting process. Since they cannot escape and are non-compressible, they recondense on or within the waste slug and create gaps and voids within the slug through which the needle points may be exposed.

It is an object of this invention to provide a device for the destruction, sterilization and encapsulation of hazardous plastic waste products, and in particular waste such as used medical syringes with attached needles, lancets, blood test strips or the like, which provides a safe and efficient means to form the plastic waste into a disposable plastic slug with the needles securely encased therein by combination of pressure and temperature. It is a further object to provide such a device which allows gas and liquids to escape from the melting chamber such that they are not retained within the waste slug. It is a further object to provide such a device which eliminates the problems associated with plastic flash by providing a melting chamber machined from a single block or cast to have no joints or seams, and which reduces the number of joints, seals and moving components required to accomplish the task in order to simplify the device. It is a further object to provide such a device in which a reciprocating compaction head for the plastic waste is constructed such that the waste slug becomes temporarily attached to the compaction head such that the plastic slug is removed from the melt chamber by retraction of the compaction head. It is a further object to provide such a device in which the compaction head is reciprocated by a rotating cam and in which the plastic slug is at least partially ejected from the compaction head by a second rotating cam.

SUMMARY OF THE INVENTION

The invention is a device for the safe destruction, sterilization and encapsulation of hazardous plastic waste, such as in particular used medical syringes with attached needles, lancets or blood test strips, comprising in general an external housing having an opening for the insertion of the plastic waste and for the removal of a compacted, sterilized plastic plug after the material has been processed. The housing contains a melt chamber, preferably generally elliptical or rectangular with rounded ends and generally relatively thin, which is accessible through the opening to receive the plastic waste. A reciprocating compaction head corresponding to the configuration of the side walls of the melt chamber is preferably operated by a motor driven cam. Heating means are provided to elevate the temperature within the melt chamber to at least 350 degrees F. in order to melt and sterilize the plastic waste. The base of the compaction head is provided with an outwardly extending shoulder or bevelled lip which does not fully encompass the compaction head, at least one end having no shoulder. A second ejection cam is provided for removal of the plastic slug from the compaction head.

Plastic waste is inserted into the melting chamber through the external opening with the compaction head in the fully raised position. The device is initiated, which lowers the compaction head to a position which closes off the external opening. The heating means then elevates the temperature within the melting chamber to approximately 410 degrees F. to melt and sterilize the plastic waste. The drive motor then rotates the drive cam to force the compaction head onto the plastic waste to its point of maximum travel. As the molten plastic waste is condensing, a portion of the waste flows past the shoulder at the base of the compaction head and solidifies. Evaporating liquids and gases also escape past the compaction head shoulder. Once the melt chamber has cooled, the drive cam retracts the compaction head from the melt chamber. The plastic waste now is in the form of a plastic slug which is attached to shoulder of the compaction head, and it too is raised from the bottom of the melt chamber. At the fully retracted position, the plastic slug is even with the external opening and comes in contact with the rotating ejection cam. The ejection cam then slides the plastic slug longitudinally from the compaction head shoulder for removal from the device.

DETAILED DESCRIPTION OF THE INVENTION

With reference to the drawings, the invention will now be described in detail with regard to the preferred embodiment and best mode. In general, the invention comprises a device for the processing of plastic waste, and in particular a device for the processing of used syringes with attached needles, lancets and blood test strips, wherein the plastic waste is processed into a safe, sterile, disposable plastic slug within which the needles are safely encapsulated.

Figure 1:
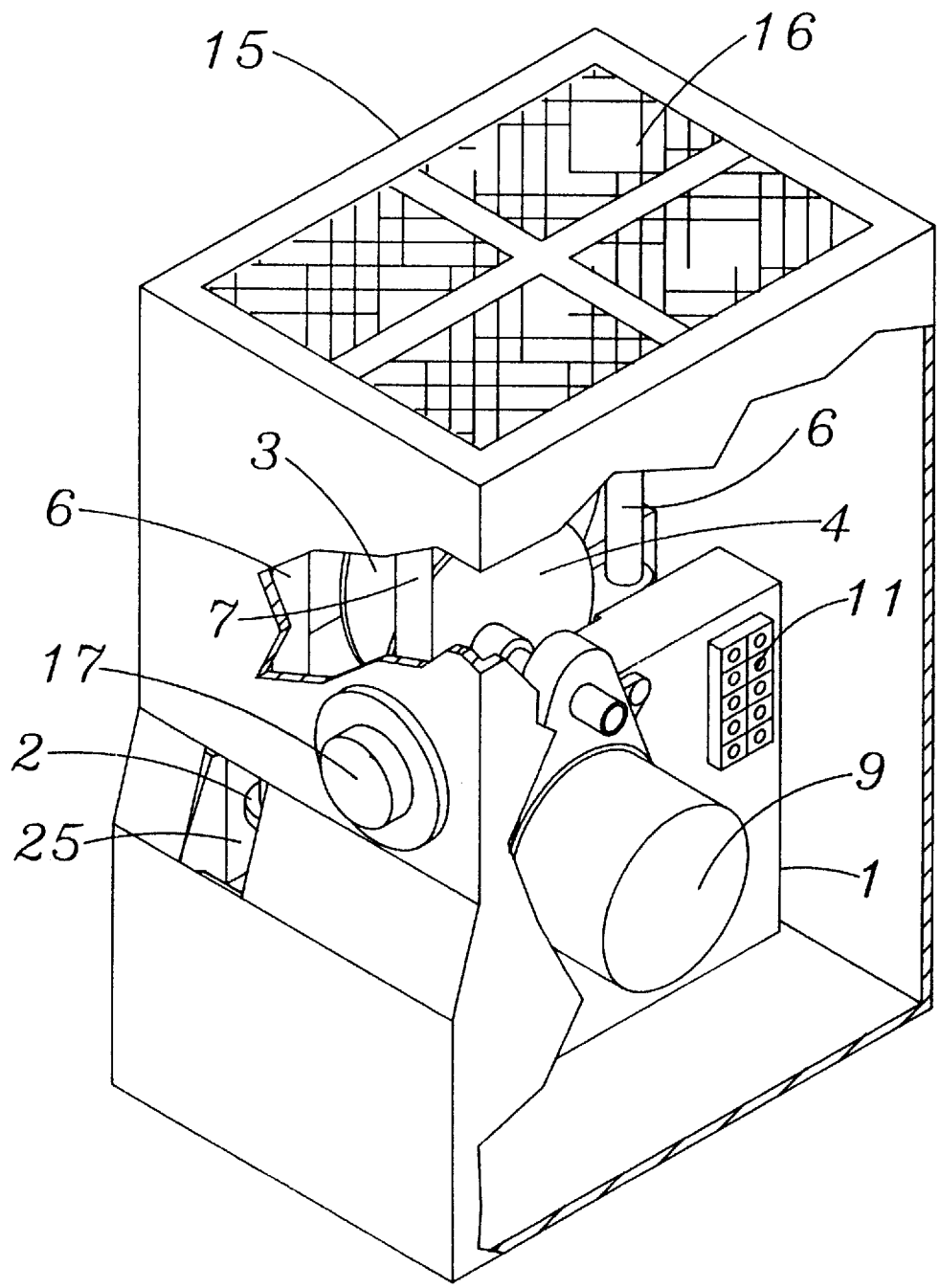
FIG. 1 is a perspective view, partially exposed, of the device.
Figure 2:
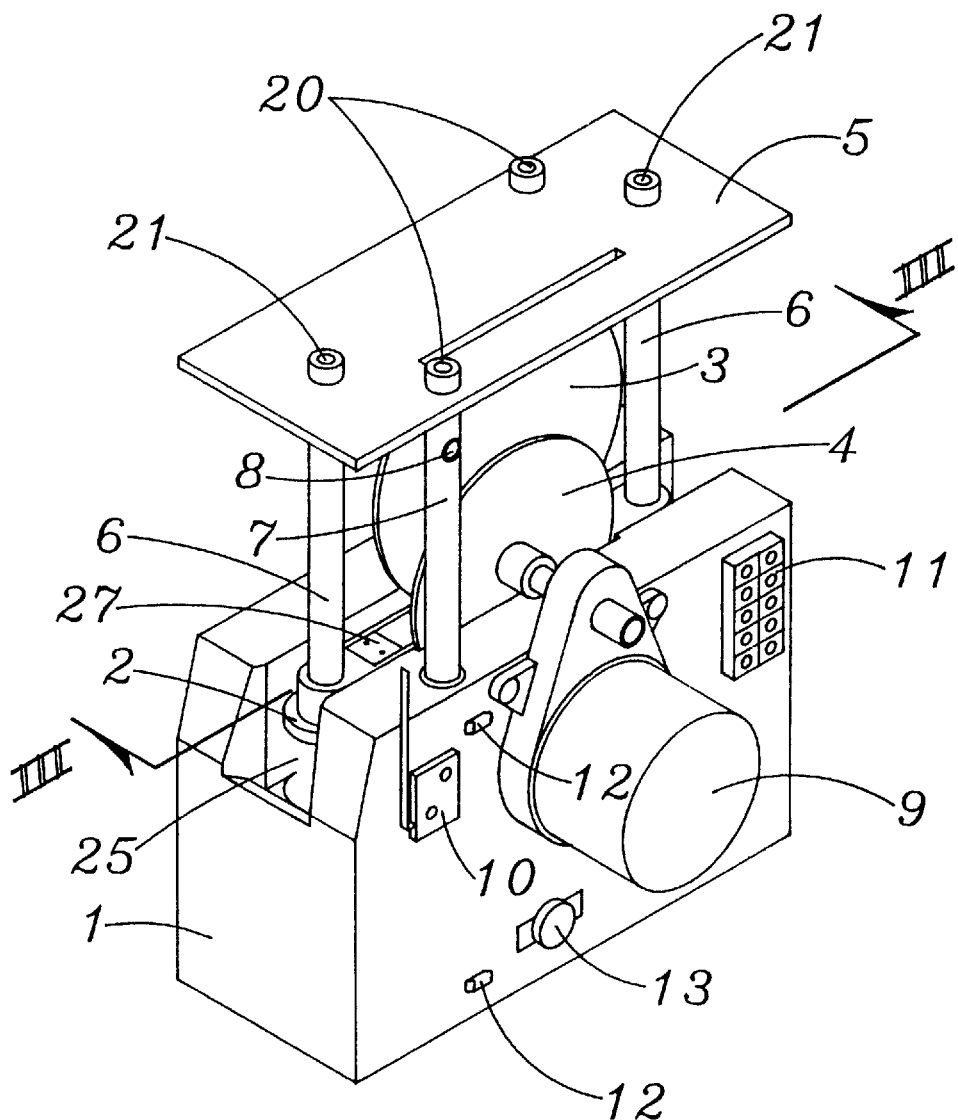
FIG. 2 is a perspective view of the device with the housing removed.

As seen in FIGS. 1 and 2, the device comprises in general a housing 15, typically formed of a suitably durable plastic or metal material, which provides a stable base for the device during operation, prevents contact with any high temperature components and provides means to vent heat and gases created during the process. Housing 15 comprises an actuation button 17 to begin the processing operation, a disposal opening 25 for insertion of the plastic waste 18 to be processed, and venting means 16, which may include filter means. The operating components, best seen in FIG. 2 where the housing 15 has been removed, comprise electrical contacts 10 responsive to the actuation button 17, a terminal board 11 with fuse to prevent overheating, means to initiate, control and deactivate the heating and reciprocating steps, here comprising microswitch 12 activated by a magnet 8, a thermostat 13 to control heating means 14, and drive motor 9 to operate drive cam 3 and ejection cam 4.

Figure 3:
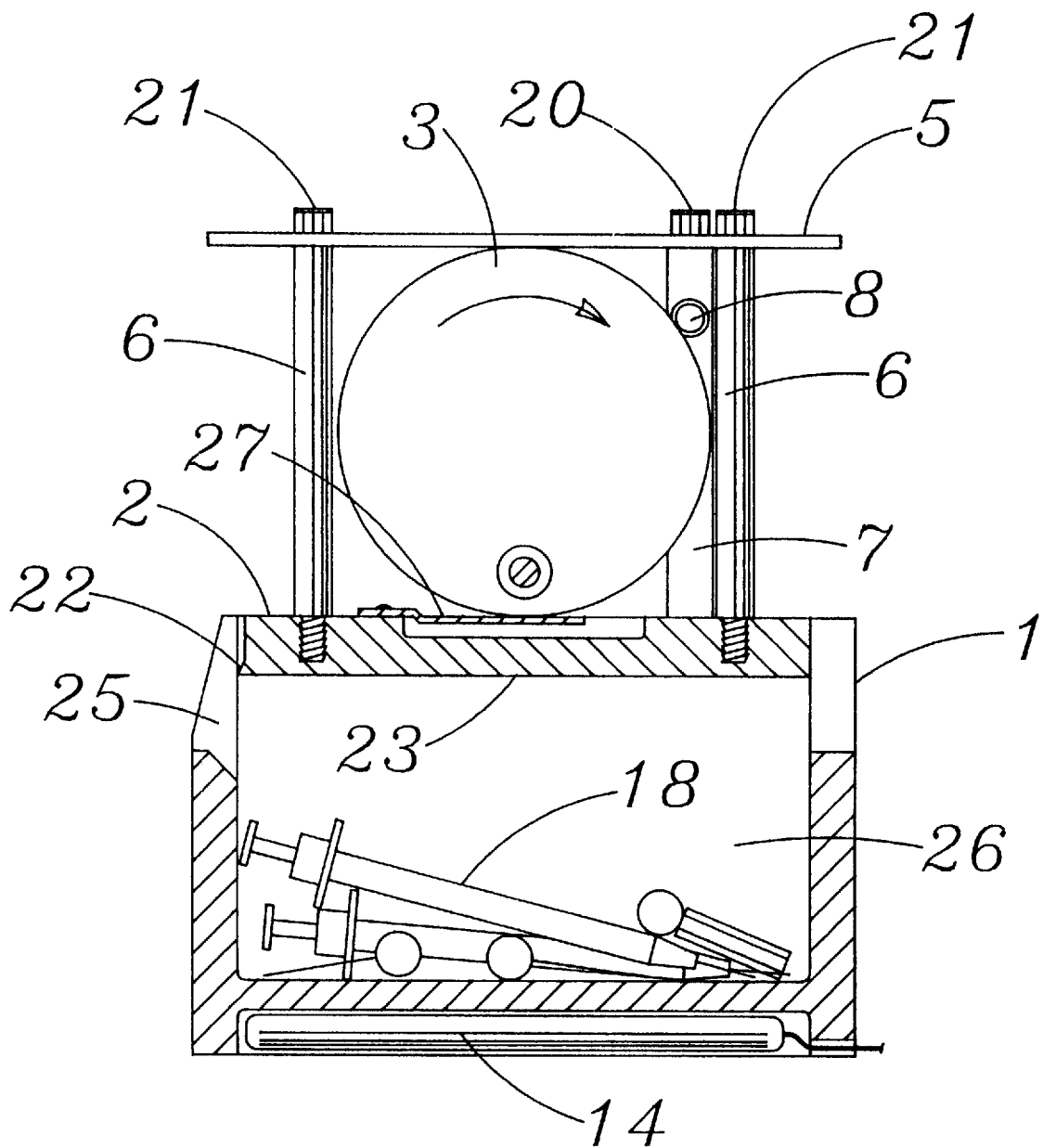
FIG. 3 is a partially exposed, partially cross-sectional view, taken along line III—III of FIG. 2, showing the operational components of the device with the compaction head in the fully retracted position.

The main block 1 of the device contains an internal melt chamber 26, preferably machined or cast from metal, ceramic, graphite or other suitable material such that there are no joints or seams. It is preferable that the melt chamber 26 have a generally elongated, rectangular configuration with rounded corners and edges at the junctions of side, end and bottom walls, such that there are no corners or angles present to undesirably position needle points. Preferably, the melt chamber 26 is sufficiently long to allow the plastic syringes with attached needles to lie horizontally within the chamber 26, as seen in FIG. 3. In the most preferred embodiment the ends of the melt chamber 26 are circular or elliptical. The disposal opening 25 communicates into a narrow end of the melt chamber 26 and allows plastic waste syringes 18 to be easily inserted needle first through the opening 25. The melt chamber 26 is of sufficient depth such that the plastic waste 18 will fall below the bottom of the disposal opening 25.

Mounted within melt chamber 26 is a reciprocating condenser or compaction head 2, configured to correspond and mate with the side and end walls of melt chamber 26. Compaction head 2 is mounted onto support rods 6 by screws 21, which connect it to a mounting plate 5.

Figure 6:
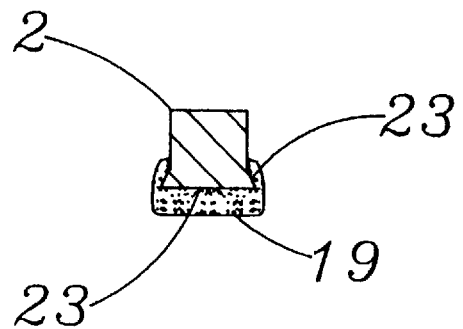
FIG. 6 is a partial cross-sectional view showing the shoulder of the compaction head with the attached waste slug.

The mounting plate 5 is connected by screws 20 to guide rods 7 which extend into the vertical receiving channels in the main block 1, thereby allowing the compaction head 2 to be reciprocated within melt chamber 26 in order to compact the plastic waste 18. In the retracted or recessed position, as shown in FIG. 3, the compaction head 2 is positioned above the bottom of the disposal opening 25 to allow insertion of the plastic waste 18 through the housing 15 and into the melt chamber 26. The compaction head 2 has a generally smooth, planar bottom surface or base 23 and a shoulder or bevelled lip 22 extending partially around the compaction head 2 at a point adjacent or near the base 23. The compaction head shoulder 22 is wider than the main portion of the compaction head 2, such that an open area is presented directly above the shoulder 22 between the compaction head 2 and side walls of the melt chamber 26 which allows the molten plastic waste 19 to flow upward between the compaction head 2 and the side walls of the melt chamber 26 and also inward above the shoulder 22 itself. The shoulder 22 may be configured as a bevelled foot, as shown in FIG. 6, or may be formed in other configurations, such as curved or rectangular in cross-section. The shoulder 22 extends over at least a portion of both of the longitudinal sides of the compaction head 2 and preferably extends around the end of the compaction head 2 adjacent the disposal opening 25. The shoulder 22 does not extend around the opposing end of the compaction head 2, as this would prevent removal of the slug 19.

Figure 4:
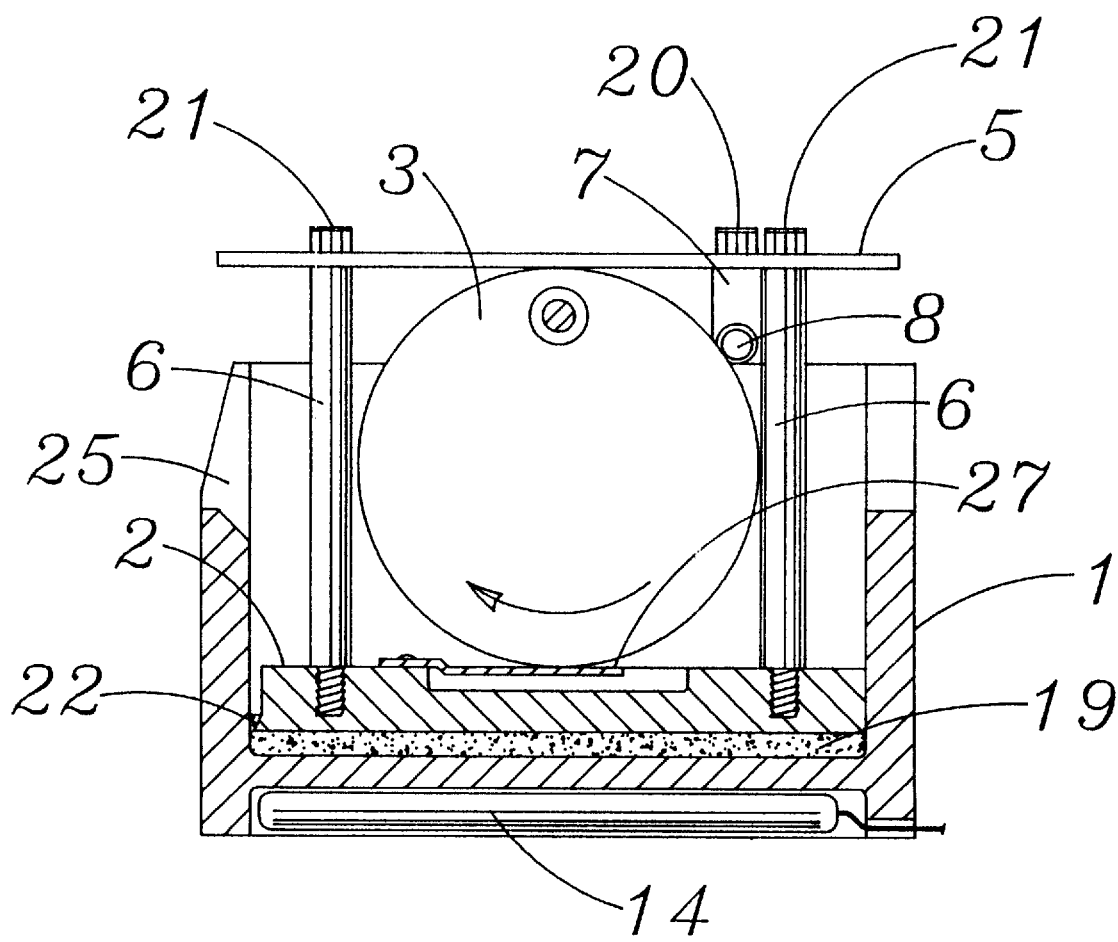
FIG. 4 is a view similar to FIG. 3, with the compaction head in the fully extended position.

The means to reciprocate the compaction head 2 preferably comprises a rotating drive cam 3 connected to a power means 9, such as a drive motor, although it is possible to substitute other known reciprocating systems, including hydraulic pistons, threaded rods, etc. The drive cam 3 is mounted between mounting plate 5 and compaction head 2, and is attached to the shaft of the drive motor 9 such that the drive cam 3 retracts compaction head 2 above the bottom of disposal opening 25 in the non-operational position, as shown in FIG. 3. As the drive cam 3 is rotated, the compaction head 2 is extended past disposal opening 25 and toward the bottom of melt chamber 26, as shown in FIG. 4. The device is designed such that compaction head 2 does not contact the bottom of melt chamber 26 even at maximum travel, thus creating a space between the bottom of the melt chamber 26 and the bottom of the compaction head 2 for formation of the plastic slug 19. The retraction position of the compaction head 2 is designed such that the shoulder 22 and bottom of the compaction head 2 is accessible through the disposal opening 25, with enough clearance to allow the plastic slug 19 to be removed from the compaction head 2.

Operationally, with the compaction head 2 in the fully retracted position, the melt chamber 26 is loaded with plastic waste 18 through disposal opening 25. The device is actuated, which causes drive motor 9 to begin rotating drive cam 3. As the compaction head 2 descends into melt chamber 26, the disposal opening 25 is sealed off such that no further plastic waste can be inserted. At this point the magnet 8 mounted in guide rod 7 deactivates drive motor 9 and activates heating element 14 in the main block 1. The melt chamber temperature is elevated to approximately 410 degrees F., at which point thermostat 13 deactivates the heating means 14 and reactivates the drive motor 9. The plastic waste 18 has now melted sufficiently to allow it to be molded under pressure. The drive cam 3 now fully extends compaction head 2 into melt chamber 26, compressing the plastic waste 18 into a plastic slug or body 19 shaped in a generally elongated, thin configuration matching the space created by the combination of the melt chamber 26 and bottom 23 of the compaction head 2. The drive motor 9 is then deactivated. When the melt chamber 26 has sufficiently cooled—e.g., to approximately 110 degrees F.—thermostat 13 reactivates drive motor 9 and the compaction head 2 is withdrawn by the continued rotation of drive cam 3.

Figure 5:
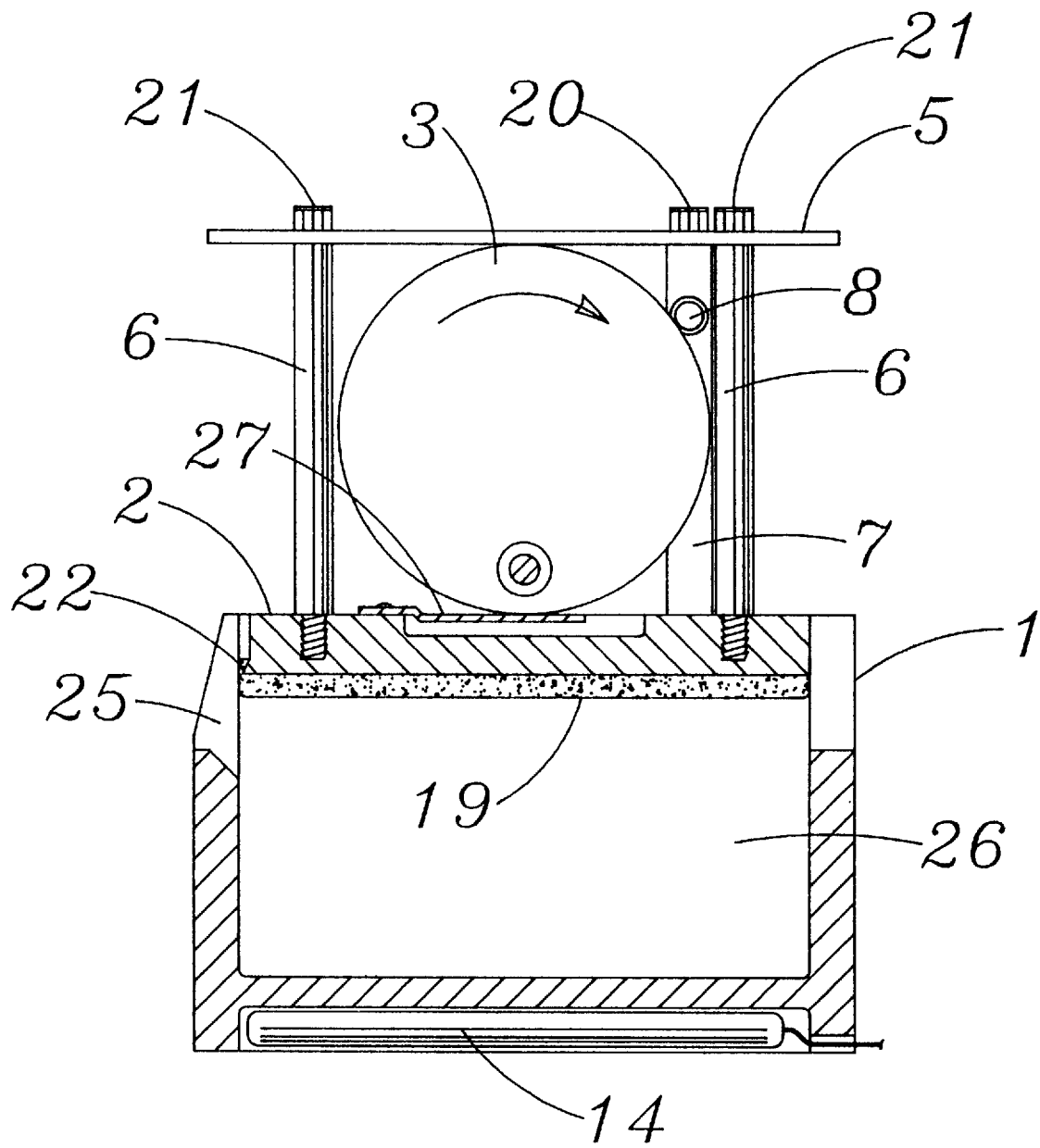
FIG. 5 is a view similar to FIG. 3, with the compaction head in the retracted position and showing the waste slug attached to the shoulder of the compaction head.

Should the volume of melted plastic waste 18 be insufficient to insure that all needles will be fully encapsulated, the plastic plug 19 compressed by the compaction head 2 will remain in the bottom of the melt chamber 26 when the compaction head is withdrawn, until more plastic waste 18 is added and the processing cycle repeated. If the plastic waste 18 when melted is of sufficient volume to insure that all needles will be fully encapsulated, a small amount of the molten plastic will be forced upward around the compaction head shoulder 22 during the extension of the compaction head, as shown in FIGS. 4 and 6. This plastic which flows through the joint between the compaction head shoulder 22 and the walls of the melt chamber 26, typically called flash in injection molding applications and considered a problem to be corrected, is used to advantage by the present invention. The plastic which flows around the compaction head shoulder 22 hardens to form a plastic flange which connects the plastic slug 19 to the bottom of the compaction head 2. In this manner, when the compaction head 2 is withdrawn, the plastic slug 19 is withdrawn along with it, as shown in FIG. 5. When the compaction head 2 is fully retracted, the plastic slug is positioned even with the disposal opening 25. Because the shoulder 22 does not extend around the far, opposite end of the compaction head 2, the plastic slug 19 containing the encapsulated needles can be pulled off compaction head 2 through disposal opening 25. The device is then ready for processing additional plastic waste 18. Alternatively, the device could be provided with a second opening opposite to the disposal opening 25 and the plastic slug 19 removed through this second opening.

Figure 7:
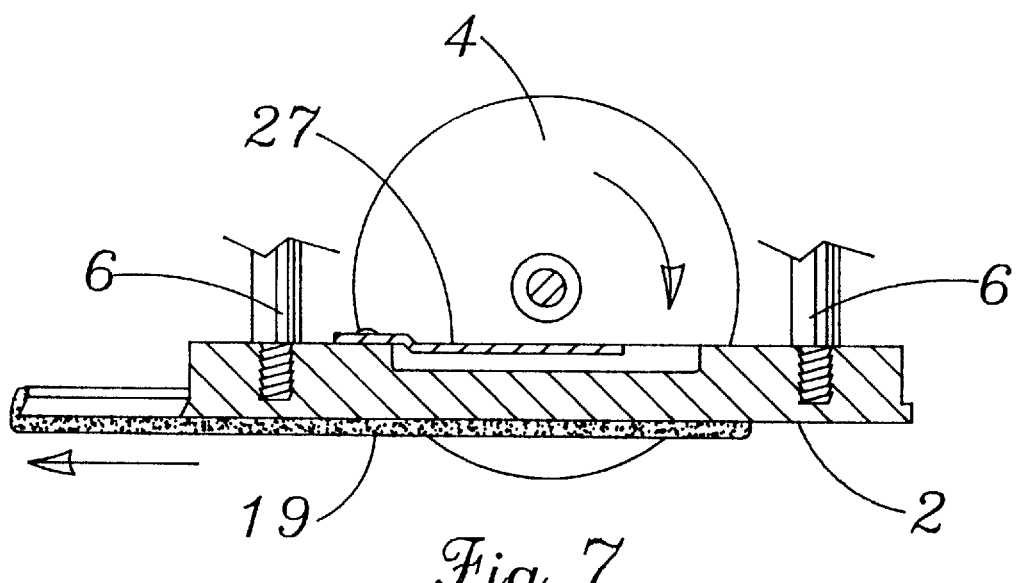
FIG. 7 is a partially exposed, partially cross-sectional view of the ejection cam, compaction head and plastic slug being ejected from the compaction head shoulder.

In preferred embodiment, the device further comprises a rotating ejection cam or plate 4 also mounted onto the shaft from drive motor 9, as shown in FIGS. 2 and 7, which rotates such that its lower portion travels in the direction of the disposal opening 25. The ejection cam 4 is positioned adjacent to the shoulder 22 of compaction head 2. As the plastic slug 19 attached to the compaction head 2 is raised, the hardened plastic flange surrounding the compaction head shoulder 22 comes into contact with the rotating ejection plate 4, sliding the plastic slug 19 outwardly from the melt chamber 26, as shown in FIG. 7. This causes the plastic slug 19 to be partially removed from the compaction head 2 and extended through disposal opening 25, where it is then completely removed manually or mechanically.

Figure 8:
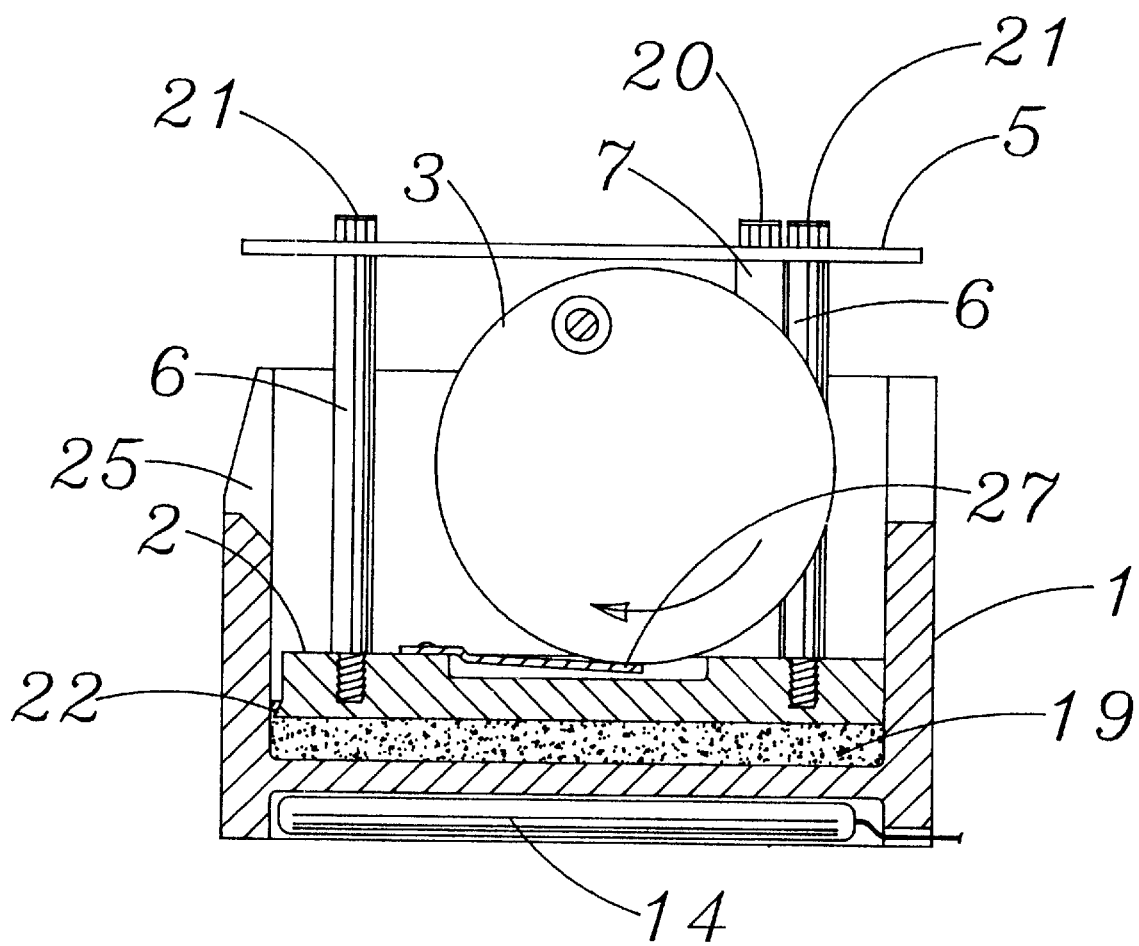
FIG. 8 is a view similar to FIG. 3 showing the operation of the relief spring when the melt chamber is overfilled.

In a further preferred embodiment, the device further comprises a overfill relief spring 27 which is mounted onto the upper side of the compaction head beneath the drive cam 3, in a manner which allows downward flexing the spring 27. The spring 27 is positioned such that the drive cam 3 extends the compaction head 2 into the melt chamber 26 by contacting the spring 27 instead of directly contacting compaction head 2. Spring 27 is composed of a sufficiently rigid material such that the normal resistance forces encountered during the compression of the molten plastic waste 18 will not be sufficient to cause it to flex. Should the melt chamber 26 be overloaded with plastic waste 18 however, as shown in FIG. 8, the relief spring 27 will flex away from the drive cam 3 when the maximum desired compression is obtained, such that the compaction head 2 will remain stationary even as the drive cam 3 continues to rotate into its fully extended position. This prevents the excess molten plastic waste 18 from being forced well above the shoulder 22 and possibly onto the upper surface of the compaction head 2—a situation which could require manual cleaning and removal of the hardened plastic slug 19.

It is understood that equivalents and substitutions for various components may be obvious to those skilled in the art, and the full scope and definition of the invention therefore is to be as set forth in the following claims.

I claim:

1. A plastic waste encapsulation device comprising:
    a melt chamber having side walls and a bottom which receives plastic waste;
    heating means to elevate the temperature within said melt chamber and melt said plastic waste;
    a compaction head which reciprocates within said melt chamber to compress said melted plastic waste into a plastic slug, the configuration of said melt compaction head being such that said plastic slug is attached to said compaction head when said plastic slug hardens; and
    power means to reciprocate said compaction head within said melt chamber.

2. The device of claim 1, where said compaction head comprises a shoulder wider than said compaction head and a generally planar base, said shoulder extending partially around and positioned adjacent said base, whereby an open area above said shoulder is defined between said compaction head and said melt chamber, and where a portion of said melted plastic can flow between said shoulder and said side walls of said melt chamber such that said plastic slug becomes attached to said compaction head upon hardening.

3. The device of claim 1, further comprising a drive cam to reciprocate said compaction head, and a drive motor to rotate said drive cam.

4. The device of claim 1, where said side walls and said bottom of said melt chamber are seamlessly joined and said melt chamber has a generally elongated, rectangular configuration with rounded edges and rounded corners.

5. The device of claim 1, where further comprising an ejection cam to remove said plastic slug from said compaction head.

6. A plastic waste syringe encapsulation device which encapsulates plastic waste syringes having attached needles within a plastic slug for safe disposal, the device comprising:
    a melt chamber having an opening into which plastic waste syringes are inserted;
    heating means to elevate the temperature within said melt chamber sufficient to melt and sterilize said plastic waste syringes;
    a compaction head having a configuration corresponding to said melt chamber;
    means to reciprocate said compaction head within said melt chamber in order to compress said plastic waste syringes into a plastic slug, whereby the configuration of said compaction head is such that said plastic slug is attached to said compaction head when said plastic slug hardens and is withdrawn from said melt chamber when said compaction head is withdrawn from said melt chamber.

7. The device of claim 6, where said means to reciprocate said compaction head comprises a drive cam.

8. The device of claim 7, further comprising means to remove said plastic slug from said compaction head.

9. The device of claim 8, where said means to remove said plastic slug from said compaction head comprises an ejection cam which slides said plastic slug through said melt chamber opening.

10. The device of claim 6, further comprising a relief spring mounted to said compaction head whereby said compaction head remains stationary during the extension phase in the event excess plastic waste syringes are placed within said melt chamber.

11. The device of claim 6, where said compaction head has a generally planar base and where the configuration of said compaction head is such that said plastic slug extends above said base between said compaction head and said melt chamber.

12. The device of claim 11, where said compaction head further comprises a shoulder extending partially around said compaction head adjacent said base.

13. A plastic waste encapsulation device which melts plastic waste and shapes the plastic waste into a hardened plastic plug for safe disposal, the device comprising:

(A) a melt chamber having an opening defined by seamlessly joining side walls and a bottom, the melt chamber having rounded corners, said opening of sufficient size to receive plastic waste;

(B) heating means to elevate the temperature within said melt chamber sufficient to melt said plastic waste;

(C) a reciprocating compaction head configured to fit within said melt chamber to compress said melted plastic waste into a plastic slug, said compaction head having a shoulder extending partially around a base, whereby melted plastic flowing between said shoulder and said side walls of said melt chamber encases said shoulder such that said plastic slug attaches to said compaction head upon hardening and is withdrawn from said melt chamber when said compaction head is withdrawn from said melt chamber;

(D) means to remove said hardened plastic slug from said compaction head by sliding said plastic slug from said shoulder; and (E) power means to reciprocate said compaction head within said melt chamber.

14. The device of claim 13, where said means to remove said hardened plastic slug from said compaction head comprises a rotating ejection cam.

15. The device of claim 13, where said power means comprises a drive motor and a rotating drive cam.

16. The device of claim 15, further comprising a relief spring mounted onto said compaction head whereby said compaction head remains stationary and said rotating drive cam continues rotating during the extension phase in the event excess plastic waste syringes are placed within said melt chamber.

17. The device of claim 13, where said shoulder extends outward from said base and defines an open area above said shoulder in combination with said side walls of said melt chamber.

* * * * *